United States Patent

Ramage

[11] Patent Number: 5,164,515

[45] Date of Patent: Nov. 17, 1992

[54] CHEMICAL COMPOUNDS

[75] Inventor: Robert Ramage, Edinburgh, Scotland

[73] Assignee: Wendstone Chemicals PLC, London, England

[21] Appl. No.: 481,688

[22] Filed: Feb. 20, 1990

Related U.S. Application Data

[63] Continuation of Ser. No. 30,399, Mar. 26, 1987, abandoned.

[51] Int. Cl.$^5$ .................. C07D 207/40; C07C 69/76; C07C 67/02; C07C 205/00
[52] U.S. Cl. .................. 548/545; 560/104; 560/255; 568/705
[58] Field of Search .............. 560/255, 104; 568/705; 548/545

[56] References Cited

U.S. PATENT DOCUMENTS

| | | | |
|---|---|---|---|
| 2,713,045 | 7/1955 | Wieland et al. | 560/32 X |
| 3,428,642 | 2/1969 | Debay et al. | 560/32 X |
| 3,769,271 | 10/1973 | Southard et al. | 560/32 X |
| 3,839,396 | 10/1974 | Otsuka et al. | 560/32 X |
| 3,948,971 | 4/1976 | Veber et al. | 560/32 X |
| 4,083,848 | 4/1978 | Itoh et al. | 560/32 X |
| 4,187,217 | 2/1980 | Hossall et al. | 560/32 X |
| 4,394,519 | 7/1983 | Carpino et al. | 560/32 |
| 4,725,680 | 2/1988 | Barcelo et al. | 558/232 X |

OTHER PUBLICATIONS

CA 92(21):180744b 1979.
CA 79(13):78312d 1973.

*Primary Examiner*—Paul J. Killos
*Attorney, Agent, or Firm*—Larson and Taylor

[57] ABSTRACT

A novel class of protecting compounds, particularly for amino acids, is based on 2,2 di nitrophenyl ethan-groups, particularly the groups wherein the nitro is in the para position. The ethyl group may be substituted, e.g. by an alkyl group, in the 1- position. Preferred compounds include the alcohol or halide which are suitable for protecting acid functional groups, and esters, including activated and substituted esters, particularly the succinimidyl ester, for protecting amine groups. The invention includes methods of manufacture and use, together with protected amino acids.

6 Claims, No Drawings

CHEMICAL COMPOUNDS

This application is a continuation of application Ser. No. 07/030,399 filed Mar. 29, 1987, now abandoned.

The present invention relates to chemical compounds, more specifically certain nitrophenyl compounds, their manufacture, their use, particularly as protecting agents in synthesis and the products (and intermediates) so made.

According to the present invention there is provided a class of novel chemical compounds having the structural formula

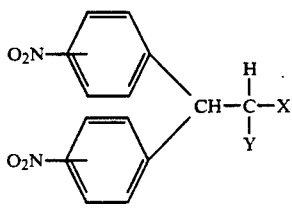

wherein the nitro groups are in the ortho or para positions, X is selected from hydroxyl, halogen and ester groups of aliphatic, aromatic and heterocyclic acids, including esters of substituted acids, and Y is selected from hydrogen and alkyl groups, including substituted alkyl.

Of the possible groups
2,2 di (4-nitrophenyl) ethan-
2,2 di (2-nitrophenyl) ethan-
2 (2-nitrophenyl) ethan-
we prefer 2,2 di (4-nitrophenyl) ethan-.

We also prefer that Y is methyl, i.e. 1-methyl, 2,2 (4-nitrophenyl) ethan- appears to be satisfactory.

Thus particularly preferred within the above class of chemical compounds are those where :
X is hydroxyl, i.e. 2,2 di (4-nitrophenyl) ethanol
X is chlorine, i.e. 2,2 di (4-nitrophenyl) ethyl chloride
X is bromine, i.e. 2,2 di (4-nitrophenyl) ethyl bromide
X is iodine, i.e. 2,2 di (4-nitrophenyl) ethyl iodide
X is a formic acid residue, i.e. 2,2 di (4-nitrophenyl) ethyl formate
X is a chloroformic acid residue, i.e. 2,2 di (nitrophenyl) ethyl chloroformate
X is an acetic acid residue, i.e. 2,2 di (nitrophenyl) ethyl acetate
X is a cinnamic acid residue, i.e. 2,2 di (nitrophenyl) ethyl cinnamate
X is a succinimido acid residue, i.e. 2,2 di (nitrophenyl) ethyl succinimidyl According to a further aspect of the present invention the said di nitrophenyl compounds are made by the nitration of 2,2 diphenyl ethyl acetate, by techniques known per se, thereby to produce 2,2 di (nitrophenyl) ethyl acetate. This compound may be further reacted to produce the other members of the above class of compounds.

Thus, for example, the nitration of 2,2 diphenyl ethyl acetate may be effected using fuming nitric acid, with concentrated sulphuric acid as a catalyst, in a solvent such as nitromethane. The compound so produced, 2.2 di (4-nitrophenyl) ethyl acetate can be hydrolysed to the alcohol by refluxing in acid conditions. The alcohol can be reacted to give the chloride by reaction with carbon tetrachloride (tetrachloro methane) and triphenyl phosphine. It can be reacted to give the bromide by reaction with tetrabromo methane, dichloro methane and triphenyl phosphine.

The chloroformate derivative can be formed by reacting the alcohol with phosgene and this may in turn be reacted with N-hydroxy succinimide in N methyl morpholine to give the succinimidyl derivative. 1 The primary utility of the compounds of the present invention is in the protection of functional groups in organic synthesis and more particularly in the protection of the functional groups of amino acids as in polypeptide synthesis.

Thus, according to yet another aspect of the present invention there is provided a protected amino acid, wherein the protecting group is a di nitrophenyl ethyl group.

In general dinitrophenyl ethyl compounds wherein the substituent X is hydroxyl or a halide are useful for the protection of acid functional groups and compounds wherein the substituent X is an activated ester are useful for the protection of amine functional groups.

Thus the products of the present invention may be used in a manner similar to 4-nitrophenyl ethyl compounds but which are also known to cleave too slowly for many purposes. Moreover, unlike the fluoroenyl methoxy carbonyl compounds which are also known as protecting agents, the compounds of the present invention are more stable and easy to store.

In general terms, the compounds of the present invention are easier to handle and can be removed more selectively and under milder conditions than previously proposed protecting groups.

We believe that the compounds of the present invention protect the acid group (or an acid group derivative) by the formation of an ester, either by reaction with the alcohol form or with the halide form. The protecting group may be removed by, for example, the use of one equivalent of diazobicyclo (4,3,0) non-5-ene (DBN) in a suitable solvent such as dichloromethane (methylene chloride) or N,N-dimethyl formamide.

Investigations showed that removal of the protecting group probably proceeded via Elcb with an activation energy of 38 +/−8 kj per mol.

The protecting group has been found to be stable in the presence, inter alia, of piperidine, N-ethyl piperidine, N-methyl morpholine, triethylamine, pyridine, sodium hydroxide, hydrochloric acid in methanol, and trifluoroacetic acid.

As an example of the use of the present invention in the preparation of a protected amino acid, alanine (amino propionic acid) can be reacted with the succinimidyl derivative to protect the amine functional group and it may then be coupled to a suitably protected peptide.

In order that the present invention may more readily be understood, certain embodiments of the same will now be described by way of example.

EXAMPLE 1

Preparation of 2,2 di (4-nitrophenyl) ethyl acetate 2 2 diphenyl ethyl acetate (144 0.6 moles) dissolved in nitromethane (200 ml). This solution then added dropwise to a stirred mixture containing fuming nitric acid (2.4 moles, 101 ml), concentrated sulphuric acid (4.8 moles, 261 ml), and nitromethane (150 ml) at −10° C. After the addition was completed, the reaction mixture was allowed to reach room temperature and stirred for an hour, after which time the reaction mixture was quenched in ice/water and extracted twice with ether and twice with ethyl acetate. The organic layers were combined and washed twice with water and twenty times with brine and finally dried over magnesium sulphate. The solvent was removed to yield a brown oil. This was triturated with diethyl ether to give a white crystalline material (yield 60%).

EXAMPLE 2

Preparation of 2,2 di (4-nitrophenyl) ethanol 2,2 di (4-nitrophenyl) ethyl acetate (30 g, 0.09 moles) produced by the process of Example 1 was dissolved in a mixture of methanol (286 ml) and concentrated hydrochloric acid (94 ml) under reflux. After three hours of reflux the reaction mixture was quenched in water to yield a yellow solid. This solid was filtered off and crystallised from toluene. The crystalline material was further recrystallised twice to provide 2,2 di (4-nitrophenyl) ethanol in pure form.

EXAMPLE 3

Preparation of 2,2 di (4-nitrophenyl) ethyl chloride 2,2 di (4-nitrophenyl) ethanol (1.354 g, 4.7 mmoles) produced by the process of Example 2 was dissolved in absolute tetrachloromethane and triphenyl phosphine (1.290 g, 4.7 mmoles) with stirring. This solution was refluxed for three hours after which time the solvent was removed under vacuum. A flash chromatography purification gave the chloride as a crystalline material (60%) which could be recrystallised from acetone.

EXAMPLE 4

Preparation of 2,2 di (4-nitrophenyl) ethyl bromide

To a stirred solution of 2,2 di (4-nitrophenyl) ethanol (0.155 g, 0.54 mmoles) produced by the process of Example 2 in carbon tetrabromide (1.08 moles, 0.362 g) was added triphenyl phosphine (21.08 mmoles, 0.289 g). The originally clear liquid turned yellow immediately, whilst thin layer chromatography indicated that no starting material was present. The solvent was removed under vacuum to give, after flash chromatography (eluent, 1:4 ethyl acetate: petrol ether), the bromide in crystalline form (yield 75%); recrystallisation was from methylene chloride.

EXAMPLE 5

Preparation of 2,2 di (4-nitrophenyl) ethyl chloroformate 2,2 di (4-nitrophenyl) ethanol (14.352 g, 49.8 mmoles) produced by the process of Example 2 was dissolved in absolute toluene (200 ml). To this solution was added with stirring phosgene, (64.4 ml, 1.5 equivs, 94.7 mmoles) as a 12.5% w/w solution in toluene at 40° C. After complete addition, N-methyl morpholine (5.5 ml, 49.8 mmoles) was added, a white precipitate forming immediately. After stirring for an hour at room temperature, the precipitate was filtered off and the solvent removed under vacuum to produce a white crystalline material (100% yield).

EXAMPLE 6

Preparation of 2,2 di (4-nitrophenyl) ethyl succinimidyl 2,2 di (4-nitrophenyl) ethyl chloroformate (17 g, 48.5 mmoles) produced by the process of Example 5 was dissolved in dioxane (50 ml) and N-hydroxy succinimide (6.173 g, 53 mmoles, 1.1 equiv.) was added to give a cloudy yellow solution which was then cooled to 0° C. and N-methyl morpholine (5.4 ml, 48.5 mmoles) was added over 30 minutes. The mixture was stirred at 0° C. for 30 minutes and at room temperature for 90 minutes, after which time the solvent was removed under high vacuum to produce a white solid. This solid was crystallised from ethyl acetate and recrystallised from acetone/ethyl acetate.

EXAMPLE 7

Preparation of a protected amino acid

Alanine (0.7824 g ,8.89 mmoles, 1.25 equivs) was dissolved in 10% aqueous sodium carbonate (18.4 ml, 17.8 mmoles). This solution was then cooled to 0° C. for ten minutes. To this solution was added in one portion with vigorous stirring 2,2 di (4-nitrophenyl) ethyl succinimidyl produced by the process of Example 6 (7.1 mmoles, 3 g) dissolved in dioxane (200 ml). This mixture was stirred for ten minutes at 0° C. and for ten minutes at room temperature, after which time the reaction mixture was quenched in water (300ml). The aqueous mixture was extracted twice with ether and twice with ethyl acetate. The aqueous phase was then acidified with concentrated hydrochloric acid to pH2, the clear solution immediately forming a cloudy suspension. The acidified solution was then extracted four times with ethyl acetate. The combined organic phases were washed twice with water, twice with brine and were finally dried over sodium sulphate. The solvent was removed under vacuum to produce a crystalline solid on trituration with petrol ether (yield 2.5g, 89%). The solid was identified as

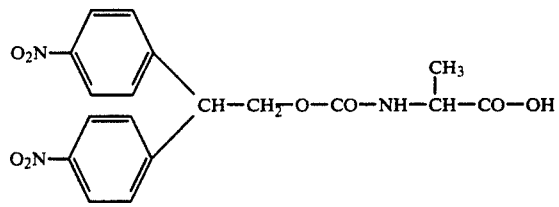

EXAMPLE 8

Preparation of a polypeptide

The protected alanine derivative produced by the process of Example 7 was dissolved in dioxan and reacted with a solution of diphenyl phosphorus oxychloride in N-methyl morpholine at 0° C. and cooled to −10° C. to produce a doubly protected alanine derivative.

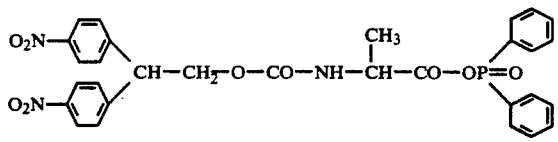

The unreacted diphenyl phosphorus oxychloride was removed and the trifluoroacetic acid salt of phenyl alanineglycine methyl ester (1 equivalent) in solution in dimethyl formamide was added at −10° C. followed by a further equivalent of N-methyl morpholine and an equivalent of 2,6 lutidine. The reaction mixture was stirred for 1 hour at 0° C. and for a further hour at room temperature.

A crystalline material was produced which proved to be a protected tripeptide in 75% yield. This material was taken up in dimethyl formamide or dichloromethane and reacted with DBN to effect removal of the protecting group and give the tripeptide

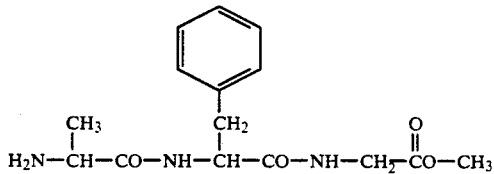

In all cases the products were characterised using NMR analysis, infra-red analysis, ultra-violet analysis, elemental analysis and mass spectrometry.

Finally, it will of course be understood that the substituted phenyl groups or the ethyl moiety may be further substituted provided that the substituents do not alter the essential characteristics of the compounds of this invention.

What is claimed is:
1. 2,2 di (4-nitrophenyl) ethanol.
2. 2,2 di (4-nitrophenyl) formate.
3. 2,2 di (4-nitrophenyl) ethyl chloroformate.
4. 2,2 di (4-nitrophenyl) ethyl acetate.
5. 2,2 di (4-nitrophenyl) ethyl cinnamate.
6. 2,2 di (4-nitrophenyl) ethyl succinimidyl.

* * * * *